(12) United States Patent
Tanaka et al.

(10) Patent No.: US 9,227,897 B2
(45) Date of Patent: Jan. 5, 2016

(54) COATING LIQUID, METHOD FOR MANUFACTURING OPTICAL COMPONENT, AND PHOTOGRAPHIC OPTICAL SYSTEM

(75) Inventors: Hiroyuki Tanaka, Kawasaki (JP);
Motokazu Kobayashi, Yokohama (JP);
Teigo Sakakibara, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 384 days.

(21) Appl. No.: 13/806,102

(22) PCT Filed: Jun. 20, 2011

(86) PCT No.: PCT/JP2011/064610
§ 371 (c)(1),
(2), (4) Date: Dec. 20, 2012

(87) PCT Pub. No.: WO2011/162400
PCT Pub. Date: Dec. 29, 2011

(65) Prior Publication Data
US 2013/0094090 A1    Apr. 18, 2013

(30) Foreign Application Priority Data

Jun. 24, 2010 (JP) ................................ 2010-144280

(51) Int. Cl.
| C07C 409/00 | (2006.01) |
| C07C 33/42 | (2006.01) |
| G02B 27/00 | (2006.01) |
| C07C 33/035 | (2006.01) |
| C07F 3/00 | (2006.01) |
| C07C 39/08 | (2006.01) |
| G02B 1/111 | (2015.01) |

(52) U.S. Cl.
CPC ............... *C07C 33/035* (2013.01); *C07C 39/08* (2013.01); *C07F 3/003* (2013.01); *G02B 1/111* (2013.01)

(58) Field of Classification Search
CPC .............................. C07C 33/035; C07C 39/08
USPC .......................................... 568/843; 359/601
See application file for complete search history.

(56) References Cited

U.S. PATENT DOCUMENTS

| 4,492,721 A | 1/1985 | Joosten |
| 5,599,588 A | 2/1997 | Poncelet |

FOREIGN PATENT DOCUMENTS

| CN | 1410588 A | 4/2003 |
| CN | 1420203 A | 5/2003 |
| CN | 1989427 A | 6/2007 |
| EP | 1150345 A2 | 10/2001 |
| JP | 2001-031681 A | 2/2001 |

OTHER PUBLICATIONS

Buchanan et al., Inorg Chem 2010, 49, 7144-7155.*
M. Tada et al., "Sol-gel processing and characterization of alkaline earth and rare-earth fluoride thin films", J. Mater. Res., vol. 14, No. 4, Apr. 1999, p. 1610 to 1616.
Buchanan,W.D.et al."Highly volatile alkaline earth metal fluoroalkoxides", Inorg Chem 2010 , 49:7144.

* cited by examiner

*Primary Examiner* — Porfirio Nazario Gonzalez
*Assistant Examiner* — Kofi Adzamli
(74) *Attorney, Agent, or Firm* — Canon U.S.A. Inc., IP Division (57) ABSTRACT

A coating liquid including a fluorine-containing organic magnesium compound represented by the following chemical formula (1), a method for manufacturing an optical component having an optical film obtained from the coating liquid, and a photographic optical system are disclosed:

$$Mg(OR_{11})(OR_{22}) \quad \text{Chemical formula (1)}$$

where $R_{11}$ represents an alkyl group that may have a substituent group having 1 or more and 6 or less carbon atoms having at least a fluorine atom, $R_{22}$ represents an alkyl group that may have a substituent group having 1 or more and 6 or less carbon atoms that may have a fluorine atom, or an aromatic cyclic group that may have a substituent group, and $R_{11}$ is different from $R_{22}$.

3 Claims, 4 Drawing Sheets

COATING LIQUID, METHOD FOR MANUFACTURING OPTICAL COMPONENT, AND PHOTOGRAPHIC OPTICAL SYSTEM

BACKGROUND OF THE INVENTION

1. Technical Field

The present invention relates to a coating liquid, a method for manufacturing an optical component, and a photographic optical system, in particular, an optical component used as a low refractive index material excellent in an antireflection effect.

2. Background Art

On a surface of an optical component constituting an optical instrument, to improve light transmittance, an antireflection film is formed.

When, in air, a low refractive index material of which refractive index nc is $$nc = \sqrt{ng} \qquad \text{(Formula 1)}$$

to the refractive index ng of a base material is coated at an optical film thickness of $\lambda/4$ to light having a wavelength $\lambda$, the refractive index theoretically becomes zero.

A general antireflection film is formed by vacuum depositing a material having the refractive index lower than that of a base material. As a low refractive index material, magnesium fluoride ($MgF_2$) having nd=1.38 is in broad use. Here, nd is the refractive index to light having a wavelength of 587 nm.

When magnesium fluoride (nd=1.38) is disposed on an optical glass BK7 (nd=1.52) at an optical film thickness of $\lambda/4$, residual reflectance of 1.26% is generated.

In this case, to nullify the reflectance, the refractive index nc is necessary to be $$nc = \sqrt{nd(BK7)} = \sqrt{1.52} = 1.23 \qquad \text{(Formula 2)}$$

As an antireflection film of an optical element necessary to have a lower reflection effect, not a single layer but a multi-layer film formed by alternately laminating a high refractive index film and a low refractive index film is used. Also in this case, a low refractive index material is important as the uppermost layer on an air side.

On the other hand, an attempt to make the refractive index smaller by forming a composite film with a low refractive index material is broadly conducted. When materials A (refractive index $n_A$) and B (refractive index $n_B$), which have different refractive indices, are mixed at a ratio of p:1–p, apparent refractive index n is represented by $$n = n_A \times p + n_B \times (1-p) = n_B - p \times (n_B - n_A) \qquad \text{(Formula 3)}$$

Herein, p represents the porosity.

It is suggested to be advantageous to form a porous film with a gas (usually, air) having the refractive index $\approx 1$ to obtain a low refractive index film. Herein, when the material A is air, $n_A \approx 1$, accordingly, formula (3) becomes $$n = n_B - p \times (n_B - 1) \qquad \text{(Formula 4)}$$

This is neither more nor less than the refractive index exhibited by a material having a bulk refractive index $n_B$ when the porosity thereof is p.

When magnesium fluoride (nd=1.38) is used as the low refractive index material to obtain a porous film having the apparent refractive index n=1.23, the porosity of about 40% is necessary.

As a method for preparing a porous film, not a dry process such as a vacuum deposition, but a wet process is effective. In the case of the wet process, after a coating material is dissolved or dispersed in a solvent, various coating methods can be used to deposit, and accordingly, there is an advantage that a porous film tends to be readily obtained.

On the other hand, examples of the methods where magnesium fluoride is prepared according to the wet process include methods illustrated below. U.S. Pat. No. 4,492,721 and M. Tada et al., J. Mater. Res., Vol. 14, No. 4, April 1999, p. 1610 to 1616 discuss a method where magnesium fluoride is prepared according to a thermal disproportional reaction. After a fluorine-containing magnesium compound or a magnesium fluorocarboxylate compound as a precursor is coated on a substrate, the thermal disproportional reaction is conducted to prepare magnesium fluoride. However, in both cases, the refractive index is around 1.39, that is, only a value of bulk magnesium fluoride is obtained. In addition, a deposition temperature thereof reaches 400° C. or 500° C.

U.S. Pat. No. 5,599,588 discusses a method for obtaining a rare earth and/or alkaline earth halide by at least hydrolyzing a halogenated alkoxide. However, since the halogenated alkoxide readily reacts with moisture in air to be instable, the deposition has to be conducted in an inert gas. Accordingly, an optical film has not been stably obtained.

As mentioned above, when a magnesium fluoride film is stably formed according to the disproportional reaction only by heating fluorine-containing organic magnesium compound, it is necessary to heat to 300° C. or more. However, there is fear of inducing deterioration of dimensional accuracy when a molded optical component is subjected to a high temperature, and, a further larger damage is inflicted depending on a material of an optical element. Accordingly, it is an issue to reduce a burning temperature.

SUMMARY OF INVENTION

The present invention is directed to a coating liquid that enables forming a low refractive index magnesium fluoride film from a fluorine-containing organic magnesium compound by a disproportional reaction that uses the heating at a temperature that does not inflict damage on an optical component.

Further, the present invention is directed to a method for manufacturing an optical component that uses the coating liquid, and to a photographic optical system.

The present inventors paid attention to a value of the acid dissociation constant (pKa) between magnesium and a fluorine-containing organic material, which constitute a fluorine-containing organic magnesium compound. When magnesium fluoride is prepared from a fluorine-containing magnesium compound, by the use of a fluorine-containing organic magnesium compound formed of a weaker acid, the thermal disproportional reaction is enabled.

However, a weak acidic fluorine-containing organic magnesium compound is instable in air, and accordingly, as it is, it is difficult to stably deposit. Further, when the weak acidic fluorine-containing organic magnesium compound is dissolved in a solvent to form a film according to a wet process, since the weak acidic fluorine-containing organic magnesium compound extremely abhors moisture, an available solvent is largely restricted.

Therefore, after studying hard, it was found that, when a structure of a fluorine-containing organic magnesium compound is rendered unsymmetrical, the fluorine-containing organic magnesium compound can be converted to magnesium fluoride by the disproportional reaction at a temperature equal to 200° C. or less even not in an inert gas atmosphere, so that the present invention came to completion.

According to an aspect of the present invention, a coating liquid includes a fluorine-containing organic magnesium compound represented by the following chemical formula (1):

Chemical formula (1)

where $R_{11}$ represents an alkyl group that may have a substituent group having 1 or more and 6 or less carbon atoms having at least one fluorine atom, $R_{22}$ represents an alkyl group that may have a substituent group having 1 or more and 6 or less carbon atoms that may have a fluorine atom, or an aromatic cyclic group that may have a substituent group, and $R_{11}$ is different from $R_{22}$.

According to another aspect of the present invention, a coating liquid includes a fluorine-containing organic magnesium compound represented by the following chemical formula (2):

Chemical formula (2)

where $R_1$ represents an alkyl group that may have a substituent group having 2 or more and 4 or less carbon atoms having at least 3 or more fluorine atoms, $R_2$ and $R_3$, respectively, represent an alkyl group that may have a substituent group having 1 or more and 4 or less carbon atoms that may have a fluorine atom, a cycloalkyl group, or an aryl group, and $R_4$ represents a hydrogen atom, an alkyl group, a cycloalkyl group, or an aryl group.

According to yet another aspect of the present invention, an optical film is an optical film prepared by coating the coating liquid on a base material to form a film, followed by burning.

According to yet another aspect of the present invention, an optical component uses the optical film.

According to an exemplary embodiment of the present invention, a coating liquid that enables forming a low refractive index magnesium fluoride film from a fluorine-containing organic magnesium compound by a disproportional reaction at a temperature that does not inflict damage on an optical component, an optical component, and a photographic optical system can be provided.

Further, according to an exemplary embodiment of the present invention, an optical component obtained from the coating liquid, and a photographic optical system can be provided.

Further features and aspects of the present invention will become apparent from the following detailed description of exemplary embodiments with reference to the attached drawings.

BRIEF DESCRIPTION OF DRAWINGS

The accompanying drawings, which are incorporated in and constitute a part of the specification, illustrate exemplary embodiments, features, and aspects of the invention and, together with the description, serve to explain the principles of the invention.

DESCRIPTION OF EMBODIMENTS

Various exemplary embodiments, features, and aspects of the invention will be described in detail below with reference to the drawings.

A coating liquid according to an exemplary embodiment of the present invention includes a fluorine-containing organic magnesium compound represented by the following chemical formula (1):

Chemical formula (1)

where $R_{11}$ represents an alkyl group that may have a substituent group having 1 or more and 6 or less carbon atoms having at least one fluorine atom, $R_{22}$ represents an alkyl group that may have a substituent group having 1 or more and 6 or less carbon atoms that may have a fluorine atom, or an aromatic cyclic group that may have a substituent group, and $R_{11}$ is different from $R_{22}$.

Further, a coating liquid according to an exemplary embodiment of the present invention includes a fluorine-containing organic magnesium compound represented by the following chemical formula (2):

Chemical formula (2)

where $R_1$ represents an alkyl group that may have a substituent group having 2 or more and 4 or less carbon atoms having at least 3 or more fluorine atoms, $R_2$ and $R_3$, respectively, represent an alkyl group that may have a substituent group having 1 or more and 4 or less carbon atoms that may have a fluorine atom, a cycloalkyl group, or an aryl group, and $R_4$ represents a hydrogen atom, an alkyl group, a cycloalkyl group, or an aryl group.

In chemical formulas (1) and (2), $R_{11}$ and $R_1$ can be $(CF_3)_2CH$ or $(CF_3)_3C$.

A compound represented by chemical formula (1) or chemical formula (2) according to an exemplary embodiment of the present invention is an asymmetric fluorine-containing organic magnesium compound. The asymmetry represents that in chemical formula (1), $R_{11} \neq R_{22}$.

When the coating liquid is coated on a base material to deposit, followed by burning, an optical component having an optical film (antireflection film) having an antireflective effect such as excellent low reflection and incident angle characteristics can be manufactured.

Specifically, when the asymmetric fluorine-containing organic magnesium compound is dissolved in various kinds of solvents and formed into a film, followed by conducting the disproportional reaction by heating, a film made of magnesium fluoride can be readily prepared, not in an inert gas atmosphere, at 200° C. or less and 150° C. or more.

In addition, a low refractive index can be realized by low temperature burning, so that, an antireflection film having an antireflective effect such as excellent low reflection and incidence angle characteristics, and an optical component therewith can be obtained. Further, when an asymmetric fluorine-containing organic magnesium compound is subjected to the disproportional reaction, an optical component having an optical film containing magnesium fluoride is prepared. Thereafter, a silicon oxide binder having affinity with a portion other than fluorine and reactivity therewith is coated on the optical film, thus-obtained optical film has a low refractive index (nd=1.1 to 1.3) and film strength that can withstand the surface scrubbing. When the binder is simultaneously coated, stability of the optical film and optical component under a high temperature and high humidity environment can be improved. This is considered that, of a prepared optical film, a portion that is not fluorinated or a portion that is instable under a high temperature and high humidity environment because of presence of other functional groups (for example, —O— or —OH) is reacted or coated with the binder, so that the stability to an environment can be improved.

In the present invention, when an asymmetric fluorine-containing magnesium compound as a fluorine-containing precursor is subjected to the disproportional reaction, a fluoride is obtained. When a fluorine-containing precursor of a metal M is represented by (M-X—F), a reaction formula is represented by

M-X—F→M-F+X.

X represents a reaction residue. Here, the reaction proceeds when (A) a fluorine atom is debonded by the disproportional reaction, (B) the fluorine atom breaks a bond between M-X, and (C) M-F is formed.

Here, it is considered that the bond strength between M-X reflects easiness of the thermal disproportional reaction. In this case, when a compound has a small acid dissociation constant, the disproportional reaction requires larger energy.

When magnesium trifluoroacetate ((CF$_3$COO)$_2$Mg) is used as a fluorine-containing organic magnesium compound used in the disproportional reaction, the acid dissociation constant (pKa) is small (pKa=0.3), and accordingly, to obtain magnesium fluoride by the disproportional reaction, the heating to 250° C. or more, more preferably to 300° C. or more is necessary.

Examples of the materials having the acid dissociation constant larger than carboxylic acids include phenols, ketones, and diketones. Among these, magnesium salts with β-diketones are preferred. When a compound made of magnesium and β-diketone is converted to asymmetric fluorine-containing organic magnesium compound having a substituent group having a larger acid dissociation constant, magnesium fluoride can be stably formed at a low temperature by the disproportional reaction.

As specific examples of the fluorine-containing organic magnesium compounds represented by chemical formula (2), examples of a part of magnesium acetylacetonates that may have a substituent group are illustrated in Table 1.

TABLE 1

| Compound Example | R1 | R2 | R3 | R4 |
|---|---|---|---|---|
| 1 | —CH(CF$_3$)$_2$ | —CH$_3$ | —CH$_3$ | —H |
| 2 | —CH(CF$_3$)$_2$ | —CF$_3$ | —CH$_3$ | —H |
| 3 | —CH(CF$_3$)$_2$ | —CF$_3$ | —CF$_3$ | —H |
| 4 | —CH(CF$_3$)$_2$ | —C(CH$_3$)$_3$ | —CH$_3$ | —H |
| 5 | —CH(CF$_3$)$_2$ | —C(CH$_3$)$_3$ | —C(CH$_3$)$_3$ | —H |
| 6 | —CH(CF$_3$)$_2$ | —CH(CH$_3$)$_2$ | —CH$_3$ | —H |
| 7 | —CH(CF$_3$)$_2$ | —CH$_3$ | —CH$_3$ | —CH$_3$ |
| 8 | —CH(CF$_3$)$_2$ | —CH$_3$ | —CH$_3$ | —C$_6$H$_5$ |
| 9 | —CH$_2$CF$_3$ | —CH$_3$ | —CH$_3$ | —H |

As compounds having a further larger acid dissociation constant, alcohols having at least fluorine can be cited. By making these compounds asymmetric, the reactivity of the disproportional reaction at low temperatures and stability to a moisture-containing atmosphere are considered to be obtained.

The fluorine-containing precursor for preparing a fluoride can contain a CF$_3$ group from the viewpoint of the easiness of fluorination by the disproportional reaction.

Examples of the fluorinated alcohols having a CF$_3$ group include 2,2,2-trifluoroethanol (CF$_3$CH$_2$OH), 1,1,1,3,3,3-hexafluoro-2-propanol ((CF$_3$)$_2$CHOH), and nonafluorotetrabutyl alcohol ((CF$_3$)$_3$COH).

In the present invention, a reaction when a fluorine-containing organic magnesium compound used in the disproportional reaction is prepared from bis(2,4-pentanedionate)magnesium (II) (compound 1) and 1,1,1,3,3,3-hexafluoro-2-propanol (HFIP) is as follows:

(A)

(Compound 1)　　　　　　　　　　　　　　　　　(Compound 2)

(B)

(Compound 2)　　　　　　　　　　　　　　　　(Compound 3)

A compound used in the disproportional reaction is (A) an asymmetric fluorine-containing organic magnesium compound (compound 2) illustrated in the right side, and a symmetric fluorine-containing organic magnesium compound (compound 3) is instable in air under the influence of the humidity.

In the present exemplary embodiment, the disproportional reaction is induced generally by heating or by burning. However, an energy line such as UV-ray also can be used. When these are combined, the disproportional reaction can be induced at lower temperatures.

The thermal disproportional reaction of the asymmetric fluorine-containing organic magnesium compound (compound 2) proceeds as illustrated below:

As illustrated with an arrow in each of the reactions (1) and (2), a fluorine atom thermally debonded from a $CF_3$ group of HFIP forms a bond with magnesium to form magnesium fluoride.

An optical film according to an exemplary embodiment of the present invention can be prepared by coating a coating liquid containing a asymmetric fluorine-containing organic magnesium compound represented by chemical formula (1) or chemical formula (2) on a base material to form a film, followed by burning.

The optical film can be constituted of magnesium fluoride.

Specifically, when a asymmetric fluorine-containing organic magnesium compound is dissolved in an organic solvent, followed by coating on an optical element, a film is formed. Examples of the methods for forming a coating film include known coating methods such as a dipping method, a spin coat method, a spray method, a printing method, a flow coat method, and a combination thereof. A film thickness can be controlled by varying a pulling speed in a dipping method or a substrate rotation speed in a spin coat method, or a concentration of a coating solution.

A film thickness of a coating film is reduced to about ½ to ¹⁄₁₀ by the disproportional reaction. A degree of reduction thereof varies depending on the condition of the disproportional reaction.

In all cases, a film thickness of the coating film is preferably controlled so that a film thickness d after the thermal disproportional reaction may be integral multiples of an optical film thickness $\lambda/4$ at a design wavelength $\lambda$.

Examples of the organic solvents include alcohols such as methanol, ethanol, propanol, isopropyl alcohol, butanol, ethylene glycol and ethylene glycol-mono-n-propyl ether; various kinds of aliphatic or alicyclic hydrocarbons such as n-hexane, n-octane, cyclohexane, cyclopentane, and cyclooctane; various kinds of aromatic hydrocarbons such as toluene, xylene, and ethyl benzene; various kinds of esters such as ethyl formate, ethyl acetate, n-butyl acetate, ethylene glycol monomethyl ether acetate, ethylene glycol monoethyl ether acetate, and ethylene glycol monobutyl ether acetate; various kinds of ketones such as acetone, methyl ethyl ketone, methyl isobutyl ketone, and cyclohexanone; various kinds of ethers such as dimethoxyethane, tetrahydrofuran, dioxane, and diisopropyl ether; various kinds of chlorinated hydrocarbons such as chloroform, methylene chloride, carbon tetrachloride, and tetrachloroethane; and non-protonic polar solvents such as N-methyl pyrrolidone, dimethyl formamide, dimethyl acetamide, and ethylene carbonate. When a coating solution used in the exemplary embodiment is prepared, among the various kinds of solvents, alcohols can be preferably used from the viewpoint of solution stability.

When a fluorine-containing organic magnesium compound is made asymmetric, even though a fluorine-containing alkoxide high in the reactivity with moisture, alcohols can be used as a solvent. These solvents can be appropriately selected according to a coating method. When a vaporization speed is too high, the coating irregularity tends to occur. In this case, a solvent low in vaporization pressure can be used to improve.

In the thermal disproportional reaction, a reaction temperature is different depending on fluorine-containing organic magnesium compounds used. In the case of magnesium acetylacetone imparted with hexafluoro-2-propanol, by heating at a temperature equal to or more than 200° C., the disproportional reaction is induced. Further, in the case of magnesium acetylacetone imparted with 2,2,2-trifluoroethanol, by heating at a temperature equal to or more than 150° C., the disproportional reaction is induced. At that time, when an atmosphere contains a fluorine compound, fluorination is further promoted to more porosify to result in low refractive index. At that time, the porosification proceeds by heating, and, a heating time is preferably ten minutes to two hours and more preferably 30 minutes to one hour.

It is also effective to further add a fluorine compound in the coating liquid to increase a fluorine compound in an atmosphere during the disproportional reaction step. Examples of the fluorine compounds added include fluoroacetylacetone or fluoroalcohols.

When a fluorine-containing precursor of metal M is represented by (M-X—F), the disproportional reaction is simplified and represented by the following formula:

F—X-M→F-M+X

Here, when (A) a fluorine atom is debonded by heating, (B) the fluorine atom breaks a bond between M-X, and (C) a reaction toward M-F proceeds.

However, this is considered that because, since a fluorine atom is high in reactivity, the reaction (B) is not necessarily induced, a fluorine atom generated according to the reaction (A) is dissipated outside of the system, so that the expected reaction (C) is not obtained. That is, it is suggested that the fluorination during the disproportional reaction step does not necessarily proceed as illustrated in the above formula.

Accordingly, when the fluorine atom generated by the reaction (A) is inhibited from dissipating, the fluorination reaction according to the disproportional reaction can be more efficiently conducted.

As a method of inhibiting fluorine atoms generated according to the reaction (A) from dissipating, it is effective to dispose a shield or also effective to separately introduce a fluorine source to promote a reaction. In addition, depending on a shape of a base material, the base material itself can be utilized as a shield. For example, in the case of a shape like a concave lens, when the concave lens is disposed with a concave surface directed downward, the same effect can be obtained.

In a portion other than the F/M, that is, a portion which is not stoichiometrically fluorinated, a functional group (for example, —O— or —OH) other than fluorine is considered present. Because of the simultaneous existence of a portion other than fluorine like this, environmental characteristics are considered deteriorated.

When a silicon oxide binder which is excellent in the affinity with a portion other than fluorine and has reactivity therewith is coated onto the resulted fluoride, followed by curing, a low refractive index optical film excellent in the mechanical strength is prepared. As a silicon oxide precursor, various kinds of silicon alkoxides, polysilazanes and polymers thereof can be used. Among these, more reactive polysilazanes are preferred.

As silicon alkoxide, the same or different lower alkyl groups such as an ethyl group, a propyl group, an isopropyl group, a butyl group, and an isobutyl group can be cited.

Examples of the polysilazanes include polysilazanes that do not substantially contain an organic group (perhydropolysilazane), polysilazanes where an alkyl group, an alkenyl group, an aryl group, a cycloalkyl group, or a group obtained by substituting a part or an entirety of hydrogen atoms bonded to a carbon atom of these groups with a substituent group is bonded to a silicon atom, polysilazanes where a hydrolytic group such as an alkoxy group is bonded to a silicon atom, and polysilazanes where an organic group such as an alkyl group is bonded to a nitrogen atom.

A curing reaction of the silicon oxide precursor can be promoted by the use of a catalyst. In the case of silicon alkoxide, an acid or base catalyst can be cited. In the case of silazane, various kinds of amine compounds or metal catalysts and compounds thereof can be used as the catalyst.

A solution obtained by diluting a silicon oxide precursor with a solvent is coated on the porous magnesium fluoride. In the case of silazane or polymer thereof, because of high reactivity, it is important to use a hydrophobic solvent. Examples of the hydrophobic solvents include petroleum solvents such as xylene or toluene, and dibutyl ether.

In the case of silazane, during dilution with a hydrophobic solvent or after dilution therewith, it is important to add a catalyst to suppress the reaction.

A solution containing a silicon oxide precursor, which is coated on the fluoride contains $SiO_2$ in terms of $SiO_2$ in the range of $0.001 \leq SiO_2 \leq 0.1$, preferably in the range of $0.005 \leq SiO_2 \leq 0.05$. In the case of $SiO_2 < 0.001$, an amount of the precursor as the binder is not sufficient, and accordingly, the mechanical strength of the resulted film is not sufficient. In the case of $SiO_2 > 0.1$, although the mechanical strength is increased, the refractive index becomes high.

Here, "in terms of silica" represents a solid content after a solution containing the silicon oxide precursor is completely reacted. When a solution containing a silicon oxide precursor at 10% by weight in terms of silica is completely reacted, a burned product made of 10% by weight of silica ($SiO_2$) can be obtained. The case where the precursor is not completely converted into $SiO_2$ like an organic modification is not contained therein.

The silicon oxide precursor is cured by heating. In the case of silazanes that have the reactivity higher than alkoxides, some of these are converted into silica at room temperature. By wetting and by heating, more dense silica can be formed.

To the optical film according to the exemplary embodiment, layers configured to give various kinds of functions thereto can be further disposed. For example, an adhesive layer or a primer layer can be disposed to improve the adhesiveness between a transparent base material and a hard coat layer. The refractive index of other layer disposed between the transparent base material and the hard coat layer like this is preferably set at an intermediate value of the refractive index of the transparent base material and the refractive index of the hard coat layer.

When the low refractive index optical film like this is used singularly or in a combination with a multilayer film in an optical component, an excellent antireflective property can be realized. In addition, since the optical film is low in the refractive index, when the optical film is used as the uppermost layer in a multilayer configuration, the interfacial reflection can be lowered and oblique incidence characteristics can be improved.

Figure 3A:
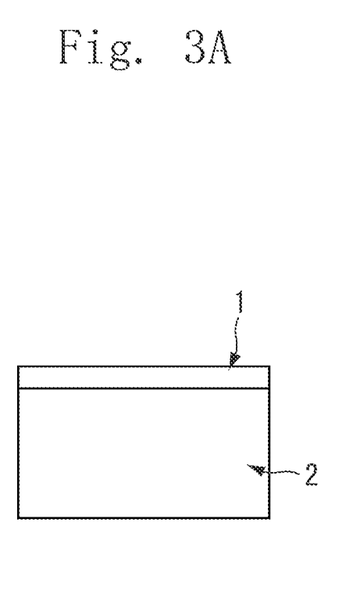
FIG. 3A is a diagram illustrating an example of an optical element according to an exemplary embodiment of the present invention.
Figure 3B:
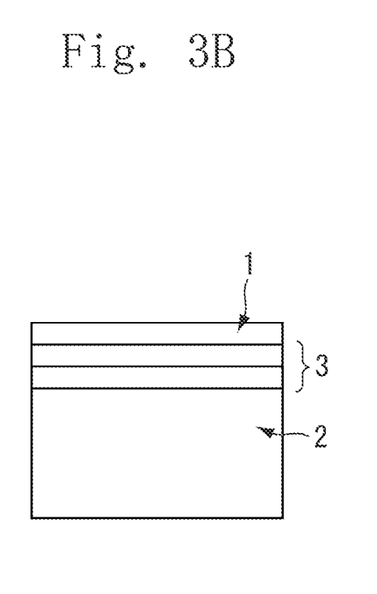
FIG. 3B is a diagram illustrating an example of an optical element according to an exemplary embodiment of the present invention.

An example of an optical component manufactured according to a method for manufacturing an optical component in an exemplary embodiment of the present invention is illustrated in FIGS. 3A and 3B. In FIG. 3A, reference numeral 1 denotes a base material and reference numeral 2 denotes an optical film obtained from a coating liquid according to an exemplary embodiment of the present invention. In FIG. 3B, reference numeral 1 denotes a base material, reference numeral 2 denotes an optical film obtained from a coating liquid according to the exemplary embodiment, and reference numeral 3 denotes an example where a multilayer film is formed between the base material and the optical film. In FIG. 3B, although an example of a two-layer film is illustrated, a single layer film or a multilayer film obtained by alternately laminating a high refractive index layer and a low refractive index layer may be used. As a film formed between the base material and the optical film, for example, inorganic compounds such as titanium oxide ($TiO_2$), silicon oxide ($SiO_2$), and magnesium fluoride ($MgF_2$), a film formed of an organic material such as various resins, organic-inorganic composite film formed by using metal alkoxide as a starting material, or the like can be used. Since the optical film obtained from a coating liquid according to the exemplary embodiment of the present invention can realize a low refractive index film, an optical film according to the exemplary embodiment of the present invention has an excellent antireflective property. In addition, since the optical film is excellent also in the mechanical strength, even if dust is attached thereto, the dust can be readily wiped, and accordingly, the optical film can be formed on the uppermost surface. The optical component according to the exemplary embodiment of the present invention can be applied to various kinds of optical components.

Figure 4:
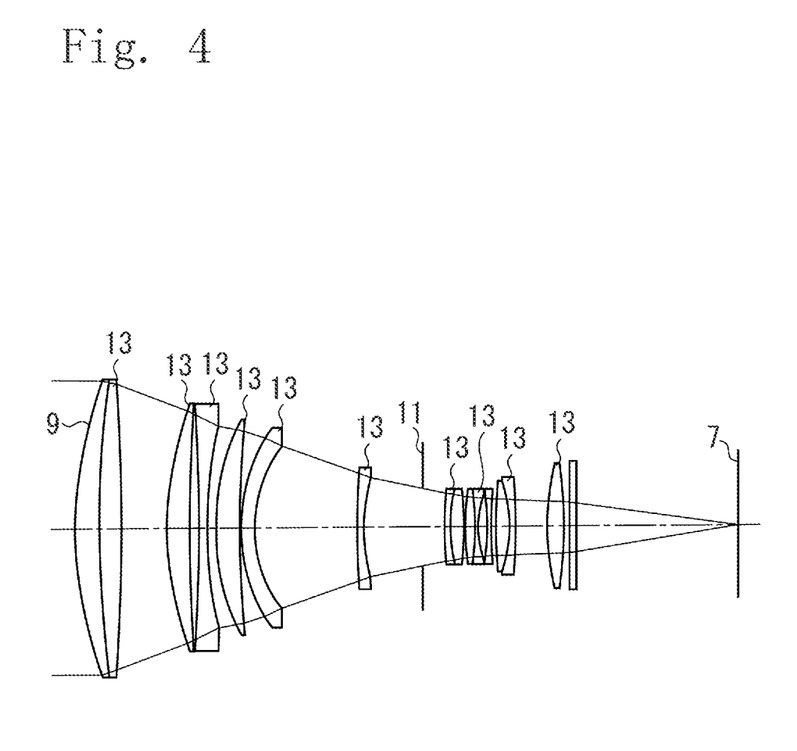
FIG. 4 is a diagram illustrating an example of a photographic optical system according to an exemplary embodiment of the present invention.

An example where the optical component manufactured according to a method for manufacturing an optical component according to the present embodiment is used in a photographic optical system is illustrated. FIG. 4 illustrates a cross-section of a photographic lens (herein, a telephoto lens is illustrated without particularly restricting thereto.) of such as a camera.

In FIG. 4, reference numeral 7 denotes a film that is an imaging surface, or a solid-state image sensor (photoelectric conversion element) such as a CCD sensor or a CMOS sensor, and reference numeral 11 denotes a stop. Reference numeral 13 denotes optical members. FIG. 4 illustrates a photographic optical system where light from an object is focused with the optical members 13, and the object image is imaged on a film or a solid-state image sensor denoted by reference numeral 7. On a surface of each of the optical members 13, an optical film is formed. In the photographic optical system according to the exemplary embodiment, of the optical members 13, at least one thereof 13 is the optical member according to the exemplary embodiment, and the optical member 13 focuses light from an object to image an object image on an image sensor. At least one of the optical films formed on the optical members 13 has the optical film obtained from a coating liquid according to the exemplary embodiment. The optical film obtained from the coating liquid according to the exemplary embodiment is low in the refractive index to have excellent antireflection performance and also excellent mechanical strength, and accordingly, the optical film is preferably formed on the frontmost surface 9.

Further, in addition thereto, the optical film can be used also in binoculars, display devices such as projectors, or window panes.

Hereinafter, the present invention will be described in detail with reference to examples.

EXAMPLE 1

[Refractive Index Measurement Sample]

A synthetic quartz substrate having a diameter of 30 mm and a thickness of 1 mm was ultrasonic cleansed with isopropyl alcohol and dried, so that a coating substrate was prepared.

To 2 parts by weight of bis(2,4-pentanedionate)magnesium (manufactured by Tokyo Kasei Kogyo Co., Ltd.) and 23 parts by weight of isopropyl alcohol, 7 parts by weight of 1,1,1,3,3,3-hexafluoro-2-propanol (manufactured by Kishida Chemical Co., Ltd., hereinafter abbreviated as HFIP) was added little by little and dissolved therein, so that a transparent coating material was prepared.

The coating material was spin coated on the quartz substrate at the rotation speed of 2000 RPM. Thereafter, in order not to damage a back surface of the quartz substrate, a hot plate set at 200° C. via an aluminum table having a gap of 1 mm was used to heat to form a film. After the film was formed, a film that cannot be peeled even when touched with a finger was formed.

With a spectroellipsometer (Trade name: M-2000D, manufactured by J. A. Woollam Japan Inc.), by polarization analysis in the wavelength range from 190 to 1000 nm, the refractive index of the resulted film was analyzed. Values of the refractive index are illustrated in Table 2.

[Measurement of Infrared Absorption Spectrum]

A film was deposited on a silicon substrate in a manner similar to the reflectance/refractive index measurement sample, dried at 100° C. for 10 minutes to remove a residual solvent, so that a sample for infrared absorption spectrum measurement was prepared. An infrared absorption spectrum of the sample was measured with a Fourier transform infrared spectrometer (manufactured by Perkin-Elmer Inc.).

Figure 1:
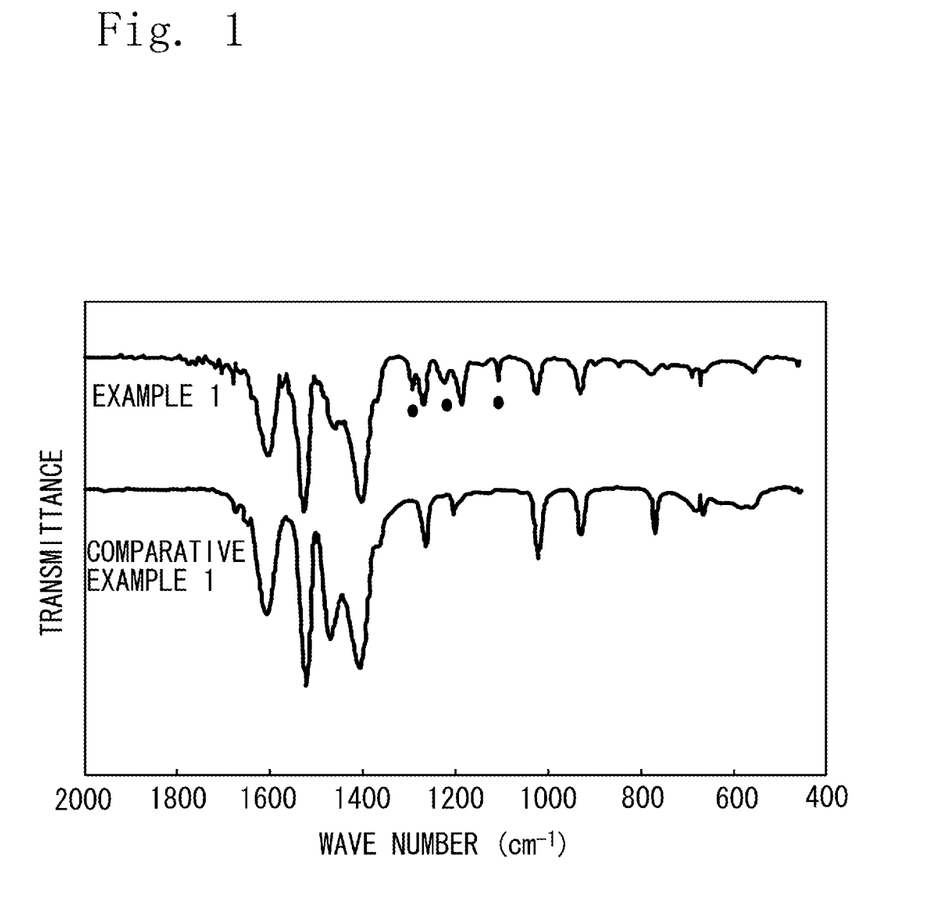
FIG. 1 is a diagram illustrating infrared spectra in Example 1 and Comparative Example 1.

FIG. 1 is a diagram illustrating infrared spectra in Example 1 and Comparative Example 1. As the result of measurement, as illustrated in FIG. 1, absorption peaks (indicated with ● in FIG. 1) different from bis(2,4-pentanedionate)magnesium (II) (Comparative Example 1) are confirmed. These peaks are derived from a C—F bond of HFIP and considered to have a structure illustrated by the following structural formula (5):

Structural formula (5)

Figure 2:
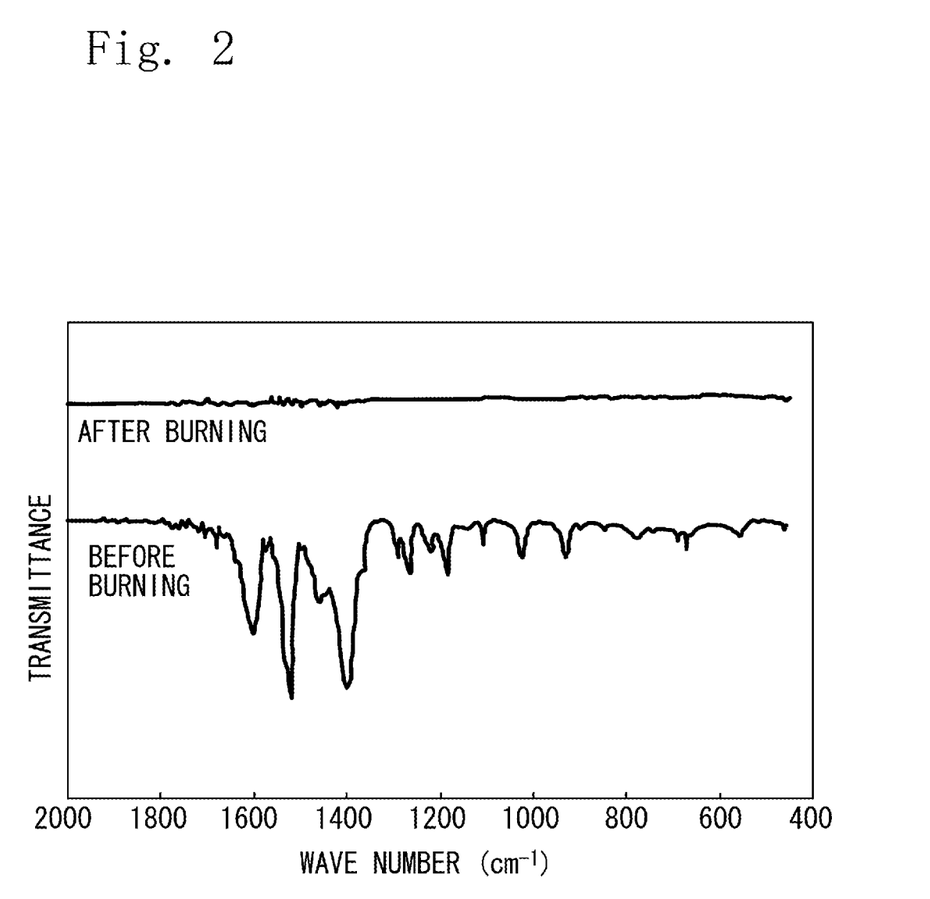
FIG. 2 is a diagram illustrating infrared spectra before and after a disproportional reaction in Example 1.

FIG. 2 is a diagram illustrating infrared absorption spectra before and after the disproportional reaction in Example 1. As illustrated in FIG. 2, it was confirmed that even when the disproportional reaction was conducted only by heating at 200° C., after the burning, almost all of the peaks derived from an organic component disappeared, that is, the sample was converted to magnesium fluoride according to the disproportional reaction at 200° C.

EXAMPLE 2

A sample was prepared and evaluated in a manner similar to Example 1 except that HFIP was changed to 2,2,2-trifluoroethanol (manufactured by Kishida Chemical Co., Ltd.).

EXAMPLE 3

A sample was prepared and evaluated in a manner similar to Example 1 except that HFIP was changed to nonafluorotetra-butyl alcohol (manufactured by Aldrich Chemical Co., Inc.).

EXAMPLE 4

A sample was prepared and evaluated in a manner similar to Example 1 except that bis(2,4-pentanedionate)magnesium (II) was changed to bis(trifluoro-2,4-pentanedionate)magnesium (II) (manufactured by Tokyo Kasei Kogyo Co., Ltd.).

EXAMPLE 5

A sample was prepared and evaluated in a manner similar to Example 1 except that bis(2,4-pentanedionate)magnesium (II) was changed to bis(hexafluoroacetylacetonate)magnesium (manufactured by Tokyo Kasei Kogyo Co., Ltd.).

EXAMPLE 6

A sample was prepared and evaluated in a manner similar to Example 1 except that magnesium (Magnesium preparation, manufactured by Aldrich Chemical Co., Inc.) and phenol were allowed to react to prepare a magnesium phenol compound, and the magnesium phenol compound was used in place of bis(2,4-pentanedionate)magnesium (II).

EXAMPLES 7 AND 8

A sample was prepared and evaluated in a manner similar to Example 2 except that the deposition temperature was changed to 180° C. or 150° C. in Example 2.

COMPARATIVE EXAMPLE 1

1 part by weight of bis(2,4-pentanedionate)magnesium (II) was dissolved in 25 parts by weight of tetrahydrofuran to prepare a coating material. The coating material was deposited on a silicon substrate in a manner similar to Example 1, followed by measuring an infrared absorption spectrum with a Fourier transform infrared spectrometer (manufactured by Perkin Elmer Inc.).

COMPARATIVE EXAMPLE 2

To 1 part by weight of magnesium powder and 18 parts by weight of 1-butanol, 25 parts by weight of trifluoroacetic acid was added little by little. After complete dissolution, a 0.20 μm filter was used to filtrate, followed by vacuum drying at 140° C., so that a transparent solid content was obtained.

2 parts by weight of the transparent solid content was dissolved in 25 parts by weight of isopropyl alcohol to prepare a coating material. The coating material was coated, deposited, and evaluated in a manner similar to Example 1. However, a coating film dried at 200° C. was not solidified.

TABLE 2

| | Compound | Deposition temperature (° C.) | Deposition | Refractive index |
|---|---|---|---|---|
| Example 1 |  | 200 | ◯ | 1.26 |
| Example 2 |  | 200 | ◯ | 1.30 |
| Example 3 |  | 200 | ◯ | 1.24 |
| Example 4 |  | 200 | ◯ | 1.25 |
| Example 5 |  | 200 | ◯ | 1.24 |
| Example 6 |  | 200 | ◯ | 1.30 |
| Example 7 | Same as Example 2 | 180 | ◯ | 1.31 |
| Example 8 | Same as Example 2 | 150 | ◯ | 1.32 |

TABLE 2-continued

| | Compound | Deposition temperature (° C.) | Deposition | Refractive index |
|---|---|---|---|---|
| Comparative Example 2 | F$_3$C—C(=O)—O—Mg—O—C(=O)—CF$_3$ | 200 | x | Not measured |

(Note 1) Deposition
○: Solidified
x: Not solidified

A coating liquid according to an exemplary embodiment of the present invention can form a low refractive index magnesium fluoride film from a fluorine-containing organic magnesium compound according to a thermal disproportional reaction at a temperature which does not inflict damage on an optical component, and accordingly, the coating liquid can be utilized to prepare an optical film of an optical component.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2010-144280 filed Jun. 24, 2010, which is hereby incorporated by reference herein in its entirety.

The invention claimed is:

1. A method for manufacturing an optical component having an optical film, the method comprising:

coating a coating liquid on a base material to form a film; and
burning the film,
wherein the coating liquid comprises:
a fluorine-containing organic magnesium compound represented by the following chemical formula (1):

$$Mg(OR_{11})(OR_{22}) \qquad \text{Chemical formula (1)}$$

where $R_{11}$ represents an alkyl group that may have a substituent group having 1 or more and 6 or less carbon atoms having at least a fluorine atom, $R_{22}$ represents an alkyl group that may have a substituent group having 1 or more and 6 or less carbon atoms that may have a fluorine atom, or an aromatic cyclic group that may have a substituent group, and $R_{11}$ is different from $R_{22}$.

2. The method according to claim 1, wherein the optical film is made of magnesium fluoride.

3. The method according to claim 1, wherein a temperature for the burning is 150° C. or more and 200° C. or less.

* * * * *